(12) United States Patent
Mosselman et al.

(10) Patent No.: US 7,060,490 B1
(45) Date of Patent: Jun. 13, 2006

(54) DNA ENCODING NOVEL ESTROGEN RECEPTOR

(75) Inventors: Sietse Mosselman, Oss (NL); Rein Dijkema, Oss (NL)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 08/826,361

(22) Filed: Mar. 26, 1997

(30) Foreign Application Priority Data

Mar. 26, 1996 (EP) .............................................. 96200820
Nov. 22, 1996 (EP) .............................................. 96203284

(51) Int. Cl.
*C12N 5/10* (2006.01)
*C12N 15/12* (2006.01)
*C12N 15/63* (2006.01)

(52) U.S. Cl. ..................... 435/320.1; 435/325; 536/23.5
(58) Field of Classification Search ................ 435/69.1, 435/325, 320.1; 536/23.5
See application file for complete search history.

(56) References Cited

U.S. PATENT DOCUMENTS

| | | | | |
|---|---|---|---|---|
| 5,508,164 A | * | 4/1996 | Kausch et al. .................. | 435/6 |
| 5,696,233 A | * | 12/1997 | Evans et al. ................ | 530/350 |
| 5,958,710 A | * | 9/1999 | Kuiper et al. | |

FOREIGN PATENT DOCUMENTS

| | | |
|---|---|---|
| EP | 0 371 820 A2 | 6/1990 |
| EP | 0 371 820 A3 | 6/1990 |
| EP | 0371820 | 6/1990 |
| EP | 0 792 292 B1 | 8/1999 |
| WO | WO97/09348 A | 3/1997 |
| WO | WO 97/09348 A3 | 3/1997 |
| WO | WO 97/09348 A2 | 3/1997 |

OTHER PUBLICATIONS

Bowie et al. (1990) Science 247: 1307–1310, Mar. 1990.*
Lin et al. (1975) Science 190:61–63, Oct. 1975.*
George et al. (1988) Macromolecular Sequencing and Synthesis Selected Methods and Applications (EQ by D.H. Schlessinger) Alan R. Liss, Inc, New york, pp. 127–149, 1998.*

Koike, S. et al., "Molecular cloning and characterization of rat estrogen receptor cDNA," *Nucleic Acids Res* 15:2499–2513 (1987).

Lees, J.A. et al., "Identification of two transactivation domains in the mouse oestrogen recpetor," *Nucleic Acids Res* 17:5477–5488 (1989).

Giguere, V. et al., "Identification of a receptor for the morphogen retinoic acid," *Nature* 330:624–629 (1987).

Enmark, E. et al., "Identification of a novel member of the nuclear receptor superfamily which is closely related to Rev–ErbA," *Biochem Biophys Res Comm* 204:49–56 (1994).

Mosselman, S. et al., "Erβ: identification and characterization of a novel human estrogen receptor," *FEBS Letters* 392:49–53 (1996).

Kuiper, G.G.J.M. et al., Cloning of a novel estrogen receptor expressed in rat prostate and ovary, *Proc Natl Acad Sci USA* 93:5925–5930 (1996).

Parker, M.G., "Nuclear receptor superfamily reunion," *TIG* 12:277–278 (1996).

G.L. Greene et al., "Sequence and Expression of Human Estrogen Receptor Complementary DNA," Science 231:1150–1154, Mar. 13, 1986.

C. Chang et al., "Human and rat TR4 orphan receptors specify a subclass of the steroid receptor superfamily," Proceedings of the National Academy of Science 91:6040–6044, Jun. 1994.

S. Mosselman et al., *FEBS Letters*, 392:1:49–53, Aug. 1996.

G.L. Grenn et al., *Science*, 231:1150–1154, Mar 13, 1986.

C. Chang et al., *Proc. Nat. Acad. Sci.*, 91:6040–6044, 1994.

R.M. Evans, *Science*, 240:889–895, May 13, 1988.

G. Kuiper et al., *Proc. Nat. Acad. Sci.*, 93:5925–5930, 1996.

* cited by examiner

*Primary Examiner*—Michael Pak
(74) *Attorney, Agent, or Firm*—Rothwell, Figg, Ernst & Manbeck, p.c.

(57) ABSTRACT

The present invention relates to isolated DNA encoding novel estrogen receptors, the proteins encoded by said DNA, chimeric receptors comprising parts of said novel receptors and uses thereof.

8 Claims, 5 Drawing Sheets

ERα

ERβ

Figure 1A:
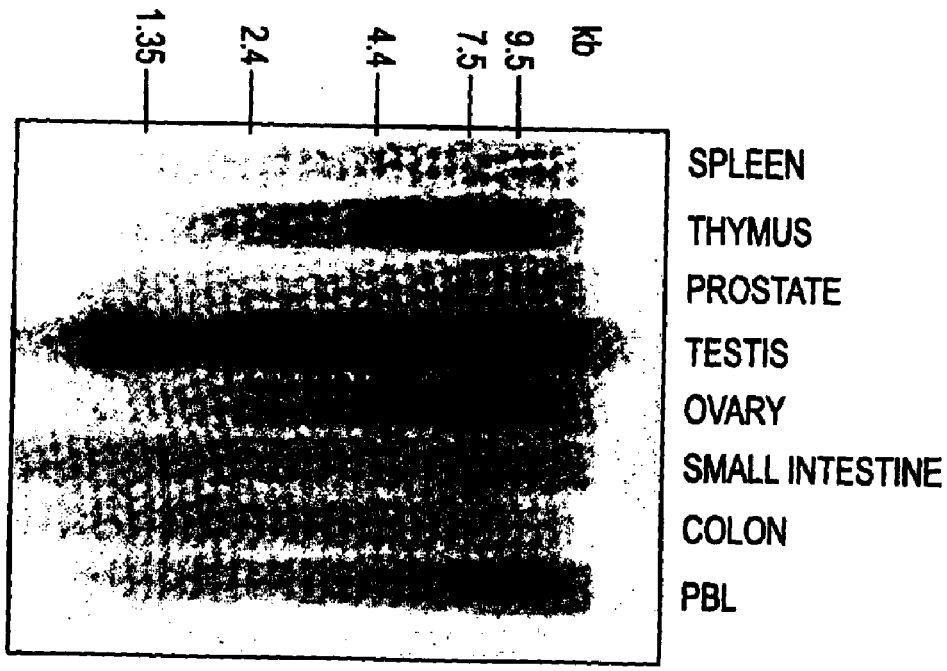

| 1. ISHIKAWA | 6. HOS | 11. Hs-760T | 16. HUV-EC-C | 21. RASMC |
|---|---|---|---|---|
| 2. HEC-1A | 7. U2-OS | 12. SW-954 | 17. BAEC-1 | bl. BLANK |
| 3. RL95-2 | 8. MG-63 | 13. Hep-G2 | 18. A10 | |
| 4. ECC-1 | 9. MCF-7 | 14. CaCo | 19. A7R5 | |
| 5. SaOS-21 | 10. T47-D | 15. HISM | 20. CavaSMC | |

DNA ENCODING NOVEL ESTROGEN RECEPTOR

This invention relates to the field of receptors belonging to the superfamily of nuclear hormone receptors, in particular to steroid receptors. The invention relates to DNA encoding a novel steroid receptor, the preparation of said receptor, the receptor protein, and the uses thereof.

Steroid hormone receptors belong to a superfamily of nuclear hormone receptors involved in ligand-dependent transcriptional control of gene expression. In addition, this superfamily consists of receptors for non-steroid hormones such as vitamin D, thyroid hormones and retinoids (Giguère et al, Nature 330, 624–629, 1987; Evans, R. M., Science 240, 889–895,1988). Moreover, a range of nuclear receptor-like sequences have been identified which encode so called d'orphan' receptors: these receptors are structurally related to and therefore classified as nuclear receptors, although no putative ligands have been identified yet (B. W. O'Malley, Endocrinology 125, 1119–1170, 1989; D. J. Mangelsdorf and R. M. Evans, Cell, 83, 841–850, 1995).

The superfamily of nuclear hormone receptors share a modular structure in which six distinct structural and functional domains, A to F, are displayed (Evans, Science 240, 889–895, 1988). A nuclear hormone receptor is characterized by a variable N-terminal region (domain A/B), followed by a centrally located, highly conserved DNA-binding domain (hereinafter referred to as DBD; domain C), a variable hinge region domain D), a conserved ligand-binding domain (herein after referred to as LBD; domain E) and a variable C-terminal region (domain F).

The N-terminal region, which is highly variable in size and sequence, is poorly conserved among the different members of the superfamily. This part of the receptor is involved in the modulation of transcription activation (Bocquel et al, Nucl. Acid Res., 17, 2581–2595, 1989; Tora et al, Cell 59, 477–487, 1989).

The DBD consists of approximately 66 to 70 amino acids and is responsible for DNA-binding activity: it targets the receptor to specific DNA sequences called hormone responsive elements (hereinafter referred to as HRE) within the transcription control unit of specific target genes on the chromatin (Martinez and Wahli, In 'Nuclear Hormone Receptors', Acad. Press, 125–153, 1991).

The LBD is located in the C-terminal part of the receptor and is primarily responsible for ligand binding activity. In this way, the LBD is essential for recognition and binding of the hormone ligand and, in addition possesses a transcription activation function, thereby determining the specificity and selectivity of the hormone response of the receptor. Although moderately conserved in structure, the LBD's are known to vary considerably in homology between the individual members of the nuclear hormone receptor superfamily (Evans, Science 240, 889–895, 1988; P. J. Fuller, FASEB J., 5, 3092–3099, 1991; Mangelsdorf et al, Cell, Vol. 83, 835–839, 1995).

Functions present in the N-terminal region, LBD and DBD operate independently from each other and it has been shown that these domains can be exchanged between nuclear receptors (Green et al, Nature, Vol. 325, 75–78, 1987). This results in chimeric nuclear receptors, such as described for instance in WO-A-8905355.

When a hormone ligand for a nuclear receptor enters the cell by diffusion and is recognized by the LBD, it will bind to the specific receptor protein, thereby initiating an allosteric alteration of the receptor protein. As a result of this alteration the ligand/receptor complex switches to a transcriptionally active state and as such is able to bind through the presence of the DBD with high affinity to the corresponding HRE on the chromatin DNA (Martinez and Wahli, 'Nuclear Hormone Receptors',125–153, Acad. Press, 1991). In this way the ligand/receptor complex modulates expression of the specific target genes. The diversity achieved by this family of receptors results from their ability to respond to different ligands.

The steroid hormone receptors are a distinct class of the nuclear receptor superfamily, characterized in that the ligands are steroid hormones. The receptors for glucocorticoids (GR), mineralcorticoids (MR), progestins (PR), androgens (AR) and estrogens (ER) are classical steroid receptors. Furthermore, the steroid receptors have the unique ability upon activation to bind to palindromic DNA sequences, the so-called HRE's, as homodimers. The GR, MR, PR and AR recognize the same DNA sequence, while the ER recognizes a different DNA sequence. (Beato et al, Cell, Vol. 83, 851–857, 1995). After binding to DNA, the steroid receptor is thought to interact with components of the basal transcriptional machinery and with sequence-specific transcription factors, thus modulating the expression of specific target genes.

Several HRE's have been identified, which are responsive to the hormone/receptor complex. These HRE's are situated in the transcriptional control units of the various target genes such as mammalian growth hormone genes (responsive to glucocorticoid, estrogen, testosterone), mammalian prolactin genes and progesterone receptor genes (responsive to Estrogen), avian ovalbumin genes (responsive to progesterone), mammalian metallothionein gene (responsive to glucocorticoid) and mammalian hepatic $\alpha_{2p}$-globulin gene (responsive to estrogen, testosterone, glucocorticoid).

The steroid hormone receptors have been known to be involved in embryonic development, adult homeostasis as well as organ physiology. Various diseases and abnormalities have been ascribed to a disturbance in the steroid hormone pathway. Since the steroid receptors exercise their influence as hormone-activated transcriptional modulators, it can be anticipated that mutations and defects in these receptors, as well as overstimulation or blocking of these receptors might be the underlying reason for the altered pattern. A better knowledge of these receptors, their mechanism of action and of the ligands which bind to said receptor might help to create a better insight in the underlying mechanism of the hormone signal transduction pathway, which eventually will lead to better treatment of the diseases and abnormalities linked to altered hormone/receptor functioning.

For this reason cDNA's of the steroid and several other nuclear receptors of several mammalians, including humans, have been isolated and the corresponding amino acid sequences have been deduced, such as for example the human steroid receptors PR, ER, GR, MR, and AR, the human non-steroid receptors for vitamin D, thyroid hormones, and retinoids such as retinol A and retinoic acid. In addition, cDNA's encoding well over 100 mammalian orphan receptors have been isolated, for which no putative ligands are known yet (Mangelsdorf et al, Cell, Vol.83, 835–839, 1995). However, there is still a great need for the elucidation of other nuclear receptors; in order to unravel the various roles these receptors play in normal physiology and pathology.

The present invention provides for such a novel nuclear receptor. More specific, the present invention provides for novel steroid receptors, having estrogen mediated activity.

Said novel steroid receptors are novel estrogen receptors, which are able to bind and be activated by, for example, estradiol, estrone and estriol.

According to the present invention it has been found that a novel estrogen receptor is expressed as an 8 kb transcript in human thymus, spleen, peripheral blood lymphocytes (PBLs), ovary and testis. Furthermore, additional transcripts have been identified. Another transcript of approximately 10 kb was identified in ovary, thymus and spleen. In testis, an additional transcript of 1.3 kb was detected. These transcripts are probably generated by alternative splicing of the gene encoding the novel estrogen receptor according to the invention.

Cloning of the cDNA's encoding the novel estrogen receptors according to the invention revealed that several splicing variants of said receptor can be distinguished. At the protein level, these variants differ only at the C-terminal part.

cDNA encoding an ER has been isolated (Green, et al, Nature 320, 134–139, 1986; Greene et al, Science 231, 1150–1154, 1986), and the corresponding amino acid sequence has been deduced. This receptor and the receptor according to the present invention, however, are distinct, and encoded for by different genes with different nucleic acid sequences. Not only do the ER of the prior art (hereinafter referred to as classical ER) and the ER according to the present invention differ in amino acid sequence, they also are located on different chromosomes. The gene encoding the classical ER is located on chromosome 6, whereas the gene encoding the ER according to the invention was found to be located on chromosome 14. The ER according to the invention furthermore distinguishes itself from the classical receptor in differences in tissue distribution, indicating that there may be important differences between these receptors at the level of estrogenic signalling.

In addition, two orphan receptors, ERRα and ERRβ, having an estrogen receptor related structure have been described (Giguère et al, Nature 331, 91–94, 1988). These orphan receptors, however, have not been reported to be able to bind estrodial or any other hormone that binds to the classical ER, and other ligands which bind to these receptors have not been found yet. The novel estrogen receptor according to the invention distinguishes itself clearly from these receptors since it was found to bind estrogens.

The fact that a novel ER according to the invention has been found is all the more surprising, since any suggestion towards the existence of additional estrogen receptors was absent in the scientific literature: neither the isolation of the classical ER nor the orphan receptors ERRα and ERRβ suggested or hinted towards the presence of additional estrogen receptors such as the receptors according to the invention. The identification of additional ER's could be a major step forward for the existing clinical therapies, which are based on the existence of one ER and as such ascribe all estrogen mediated abnormalities and/or diseases to this one receptor. The receptors according to the invention will be useful in the development of hormone analogs that selectively activate either the classical ER or the novel estrogen receptor according to the invention. This should be considered as one of the major advantages of the present invention.

Thus, in one aspect, the present invention provides for isolated cDNA encoding a novel steroid receptor. In particular, the present invention provides for isolated cDNA encoding a novel estrogen receptor.

According to this aspect of the present invention, there is provided an isolated DNA encoding a steroid receptor protein having an N-terminal domain, a DNA-binding domain and a ligand-binding domain, wherein the amino acid sequence of said DNA-binding domain of said receptor protein exhibits at least 80% homology with the amino acid sequence shown in SEQ ID NO:3, and the amino acid sequence of said ligand-binding domain of said receptor protein exhibits at least 70% homology with the amino acid sequence shown in SEQ ID NO:4.

In particular, the isolated DNA encodes a steroid receptor protein having an N-terminal domain, a DNA-binding domain and a ligand-binding domain, wherein the amino acid sequence of said DNA-binding domain of said receptor protein exhibits at least 90%, preferably 95%, more preferably 98%, most preferably 100% homology with the amino acid sequence shown in SEQ ID NO:3.

More particularly, the isolated DNA encodes a steroid receptor protein having an N-terminal domain, a DNA-binding domain and a ligand-binding domain , wherein the amino acid sequence of said ligand-binding domain of said receptor protein exhibits at least 75%, preferably 80%, more preferably 90%, most preferably 100% homology with the amino acid sequence shown in SEQ ID NO:4.

A preferred isolated DNA according to the invention encodes a steroid receptor protein having the amino acid sequence shown in SEQ ID NO:5, SEQ ID NO:6, SEQ ID NO:21 or SEQ ID NO:25.

A more preferred isolated DNA according to the invention is an isolated DNA comprising a nucleotide sequence shown in SEQ ID NO:1, SEQ ID NO:2, SEQ ID NO:20 or SEQ ID NO:24.

The DNA according to the invention may be obtained from cDNA. Alternatively, the coding sequence might be genomic DNA, or prepared using DNA synthesis techniques.

The DNA according to the invention will be very useful for in vivo expression of the novel receptor proteins according to the invention in sufficient quantities and in substantially pure form.

In another aspect of the invention, there is provided for a steroid receptor comprising the amino acid sequence encoded by the above described DNA molecules.

The steroid receptor according to the invention has an N-terminal domain, a DNA-binding domain and a ligand-binding domain, wherein the amino acid sequence of said DNA-binding domain of said receptor exhibits at least 80% homology with the amino acid sequence shown in SEQ ID NO:3, and the amino acid sequence of said ligand-binding domain of said receptor exhibits at least 70% homology with the amino acid sequence shown in SEQ ID NO:4.

In particular, the steroid receptor according to the invention has an N-terminal domain, a DNA-binding domain and a ligand-binding domain, wherein the amino acid sequence of said DNA-binding domain of said receptor exhibits at least 90%, preferably 95%, more preferably 98%, most preferably 100% homology with the amino acid sequence shown in SEQ ID NO:3.

More particular, the steroid receptor according to the invention has an N-terminal domain, a DNA-binding domain and a ligand-binding domain, wherein the amino acid sequence of said ligand-binding domain of said receptor exhibits at least 75%, preferably 80%, more preferably 90%, most preferably 100% homology with the amino acid sequence shown in SEQ ID NO:4.

It will be clear for those skilled in the art that also steroid receptor proteins comprising combined DBD and LBD preferences and DNA encoding such receptors are subject of the invention.

Preferably, the steroid receptor according to the invention comprises an amino acid sequence shown in SEQ ID NO:5, SEQ ID NO:6, SEQ ID NO:21 or SEQ ID NO:25.

Also within the scope of the present invention are steroid receptor proteins which comprise variations in the amino acid sequence of the DBD and LBD without loosing their respective DNA-binding or ligand-binding activities. The variations that can occur in those amino acid sequences comprise deletions, substitutions, insertions, inversions or additions of (an) amino acid(s) in said sequence, said variations resulting in amino acid difference(s) in the overall sequence. It is well known in the art of proteins and peptides that these amino is acid differences lead to amino acid sequences that are different from, but still homologous with the native amino acid sequence they have been derived from.

Amino acid substitutions that are expected not to essentially alter biological and immunological activities, have been described in for example Dayhof, M. D., Atlas of protein sequence and structure, Nat. Biomed. Res. Found., Washington D.C., 1978, vol. 5, suppl. 3. Amino acid replacements between related amino acids or replacements which have occurred frequently in evolution are, inter alia Ser/Ala, Ser/Gly, Asp/Gly, Arg/Lys, Asp/Asn, Ile/Val. Based on this information Lipman and Pearson developed a method for rapid and sensitive protein comparison (Science 227, 1435–1441, 1985) and determining the functional similarity between homologous polypeptides.

Variations in amino acid sequence of the DBD according, to the invention resulting in an amino acid sequence that has at least 80% homology with the sequence of SEQ ID NO:3 will lead to receptors still having sufficient DNA binding activity.

Variations in amino acid sequence of the LBD according to the invention resulting in an amino acid sequence that has at least 70% homology with the sequence of SEQ ID NO:4 will lead to receptors still having sufficient ligand binding activity.

Homology as defined herein is expressed in percentages, determined via PCGENE. Homology is calculated as the percentage of identical residues in an alignment with the sequence according to the invention. Gaps are allowed to obtain maximum alignment.

Comparing the amino acid sequences of the classical ER and the ER's according to the invention revealed a high degree of similarity within their respective DBD's. The conservation of the P-box (amino acids E-G-X-X-A) which is responsible for the actual interactions of the classical ER with the target DNA element (Zilliacus et al., Mol. Endo. 9, 389, 1995; Glass, End. Rev. 15, 391, 1994), is indicative for a recognition of estrogen responsive elements (ERE's) by the ER's according to the invention. The receptors according to the invention indeed showed ligand-dependent transactivation on ERE-containing reporter constructs. Therefore, the classical ER and the novel ER's according to the invention may have overlapping target gene specificities. This could indicate that in tissues which co-express both respective ER's, these receptors compete for ERE's. The ER's according to the invention may regulate transcription of target genes differently from classical ER regulation or could simply block classical ER functioning by occupying estrogen responsive elements. Alternatively, transcription might be influenced by heterodimerization of the different receptors.

Thus, a preferred steroid receptor according to the invention comprises the amino acid sequence E-G-X-X-A within the P box of the DNA binding domain, wherein X stands for any amino acid. Also within the scope of the invention is isolated DNA encoding such a receptor.

Methods to prepare the receptors according to the invention are well known in the art (Sambrook et al., Molecular Cloning: a Laboratory Manual, Cold Spring Harbor Laboratory Press, Cold Spring Harbor, 1989). The most practical approach is to produce these receptors by expression of the DNA encoding the desired protein.

A wide variety of host cell and cloning vehicle combinations may be usefully employed in cloning the nucleic acid sequence coding for the receptor of the invention. For example, useful cloning vehicles may include chromosomal, non-chromosomal and synthetic DNA sequences such as various known bacterial plasmids and wider host range plasmids and vectors derived from combinations of plasmids and phage or virus DNA. Useful hosts may include bacterial hosts, yeasts and other fungi, plant or animal hosts, such as Chinese Hamster Ovary (CHO) cells or monkey cells and other hosts.

Vehicles for use in expression of the ligand-binding domain of the present invention will further comprise control sequences operably linked to the nucleic acid sequence coding for the ligand-binding domain. Such control sequences generally comprise a promoter sequence and sequences which regulate and/or enhance expression levels. Furthermore an origin of replication and/or a dominant selection marker are often present in such vehicles. Of course control and other sequences can vary depending on the host cell selected.

Techniques for transforming or transfecting host cells are quite known in the art (see, for instance, Sambrook et al., Molecular Cloning: A Laboratory Manual, Cold Spring Harbor Laboratory, 1989).

Recombinant expression vectors comprising the DNA of the invention as well as cells transformed with said DNA or said expression vector also form part of the present invention.

In a further aspect of the invention, there is provided for a chimeric receptor protein having an N-terminal domain, a DNA-binding domain, and a ligand-binding domain, characterized in that at least one of the domains originates from a receptor protein according to the invention, and at least one of the other domains of said chimeric protein originates from another receptor protein from the nuclear receptor superfamily, provided that the DNA-binding domain and the ligand-binding domain of said chimeric receptor protein originate from different proteins.

In particular, the chimeric receptor according to the invention comprises the LBD according to the invention, said LBD having an amino acid sequence which exhibits at least 70% homology with the amino acid sequence shown in SEQ ID NO:4. In that case the N-terminal domain and DBD should be derived from another nuclear receptor, such as for example PR. In this way a chimeric receptor is constructed which is activated by a ligand of the ER according to the invention and which targets a gene under control of a progesterone responsive element. The chimeric receptors having a LBD according to the invention are useful for the screening of compounds to identify novel ligands or hormone analogs which are able to activate an ER according to the invention.

In addition, chimeric receptors comprising a DBD according to the invention, said DBD having an amino acid sequence exhibiting at least 80% homology with the amino acid sequence shown in SEQ ID NO:3, and a LBD and, optionally, an N-terminal domain derived from another nuclear receptor, can be successfully used to identify novel ligands or hormone analogs for said nuclear receptors. Such chimeric receptors are especially useful for the identification of the respective ligands of orphan receptors.

Since steroid receptors have three domains with different functions, which are more or less independent, it is possible that all three functional domains have been derived from different members of the steroid receptor superfamily.

Molecules which contain parts having a different origin are called chimeric. Such a chimeric receptor comprising the ligand-binding domain and/or the DNA-binding domain of the invention may be produced by chemical linkage, but most preferably the coupling is accomplished at the DNA level with standard molecular biological methods by fusing the nucleic acid sequences encoding the necessary steroid receptor domains. Hence, DNA encoding the chimeric receptor proteins according to the invention are also subject of the present invention.

Such chimeric proteins can be prepared by transfecting DNA encoding these chimeric receptor proteins to suitable host cells and culturing these cells under suitable conditions.

It is extremely practical if, next to the information for the expression of the steroid receptor, also the host cell is transformed or transfected with a vector which carries the information for a reporter molecule. Such a vector coding for a reporter molecule is characterized by having a promoter sequence containing one or more hormone responsive elements (HRE) functionally linked to an operative reporter gene. Such a HRE is the DNA target of the activated steroid receptor and, as a consequence, it enhances the transcription of the DNA coding for the reporter molecule. In in vivo settings of steroid receptors the reporter molecule comprises the cellular response to the stimulation of the ligand. However, it is possible in vitro to combine the ligand-binding domain of a receptor to the DNA binding domain and transcription activating domain of other steroid receptors, thereby enabling the use of other HRE and reporter molecule systems. One such a system is established by a HRE presented in the MMTV-LTR (mouse mammary tumor virus long terminal repeat sequence in connection with a reporter molecule like the firefly luciferase gene or the bacterial gene for CAT (chloramphenicol transferase). Other HRE's which can be used are the rat oxytocin promotor, the retinoic acid responsive element, the thyroid hormone responsive element, the estrogen responsive element and also synthetic responsive elements have been described (for instance in Fuller, ibid, page 3096). As reporter molecules next to CAT and luciferase β-galactosidase can be used.

Steroid hormone receptors and chimeric receptors according to the present invention can be used for the in vitro identification of novel ligands or hormonal analogs. For this purpose binding studies can be performed with cells transformed with DNA according to the invention or an expression vector comprising DNA according to the invention, said cells expressing the steroid receptors or chimeric receptors according to the invention.

The novel steroid hormone receptor and chimeric receptors according to the invention as well as the ligand-binding domain of the invention, can be used in an assay for the identification of functional ligands or hormone analogs for the nuclear receptors.

Thus, the present invention provides for a method for identifying functional ligands for the steroid receptors and chimeric receptors according to the invention, said method comprising the steps of a) introducing into a suitable host cell 1) DNA or an expression vector according to the invention, and 2) a suitable reporter gene functionally linked to an operative hormone response element, said HRE being able to be activated by the DNA-binding domain of the receptor protein encoded by said DNA;

b) bringing the host cell from step a) into contact with potential ligands which will possibly bind to the ligand-binding domain of the receptor protein encoded by said DNA from step a);

c) monitoring the expression of the receptor protein encoded by said reporter gene of step a).

If expression of the reporter gene is induced with respect to basic expression (without ligand), the functional ligand can be considered as an agonist; if expression of the reporter gene remains unchanged or is reduced with respect to basic expression, the functional ligand can be a suitable (partial) antagonist.

For performing such kind of investigations host cells which have been transformed or transfected with both a vector encoding a functional steroid receptor and a vector having the information for a hormone responsive element and a connected reporter molecule are cultured in a suitable medium. After addition of a suitable ligand, which will activate the receptor the production of the reporter molecule will be enhanced, which production simply can be determined by assays having a sensitivity for the reporter molecule. See for instance WO-A-8803168. Assays with known steroid receptors have been described (for instance S. Tsai et al., Cell 57, 443, 1989; M. Meyer et al., Cell 57, 433, 1989).

LEGENDS TO THE FIGURES

FIGS. 1A–1B

Figure 1B:
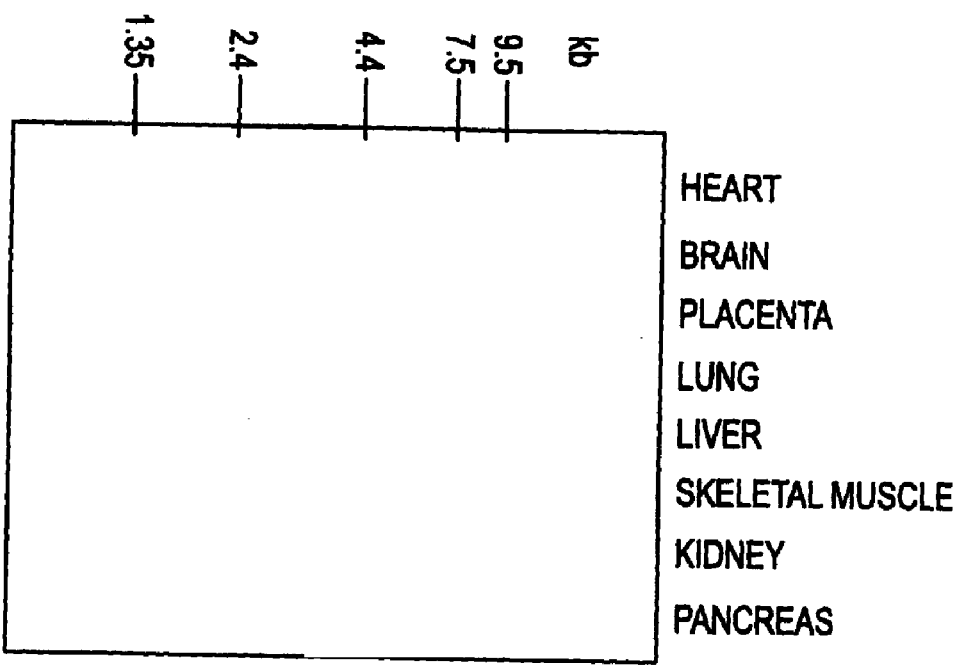

Northern analysis of the novel estrogen receptor (ERβ). Two different multiple tissue Northern blots (Clontech) (FIGS. 1A and 1B) were hybridized with a specific probe for ERβ(see examples). Indicated are the human tissues from which the RNA originated and the position of the size markers in kilobases (kb).

FIG. 2.

Histogram showing the 3- to 4-fold stimulatory effect of 17β-estradiol, estriol and estrone on the luciferase activity mediated by ERβ. An expression vector encoding ERβ was transiently transfected into CHO cells together with a reporter construct containing the rat oxytocin promoter in front of the firefly luciferase encoding sequence (see examples).

FIG. 3.

Effect of 17β-estradiol (E2) alone or in combination with the anti-estrogen ICI-164384 (ICI) on ERα and ERβ. Expression constructs for ERα (the classical ER) and ERβ were transiently transfected into CHO cells together with the rat oxytocin promoter-luciferase reporter construct described in the examples. Luciferase activities were determined in triplicate and normalised for transfection efficiency by measuring β-galactosidase in the same lysate.

FIG. 4.

Expression of ERα and ERβ in a number of cell lines determined by RT-PCR analysis (see examples). The cell lines used were derived from different tissues/cell types: endometrium (ECC1, Ishikawa, HEC-1A, RL95-2); osteosarcoma (SAOS-2, U2-OS, HOS, MG63); breast tumours (MCF-7, T47D), endothelium (HUV-EC-C, BAEC-1); smooth muscle (HISM, PAC-1, A7R5, A10, RASMC, CavaSMC); liver (HepG2); colon (CaCo2); and vagina (Hs-760T, SW-954).

All cell lines were human except for PAC-1, A7R5, A10 and RASMC which are of rat origin, BAEC-1 which is of bovine origin and CavaSMC which is of guinea pig origin.

FIGS. 5A–C

Figure 5A:
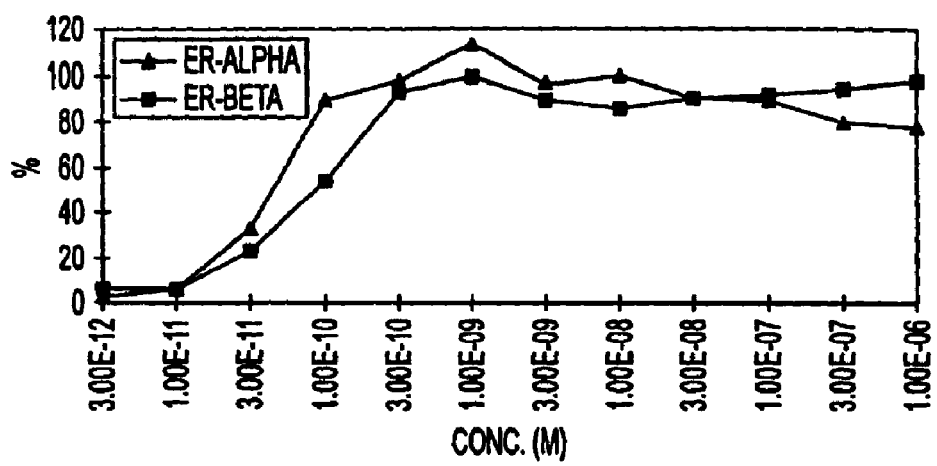
Figure 5B:
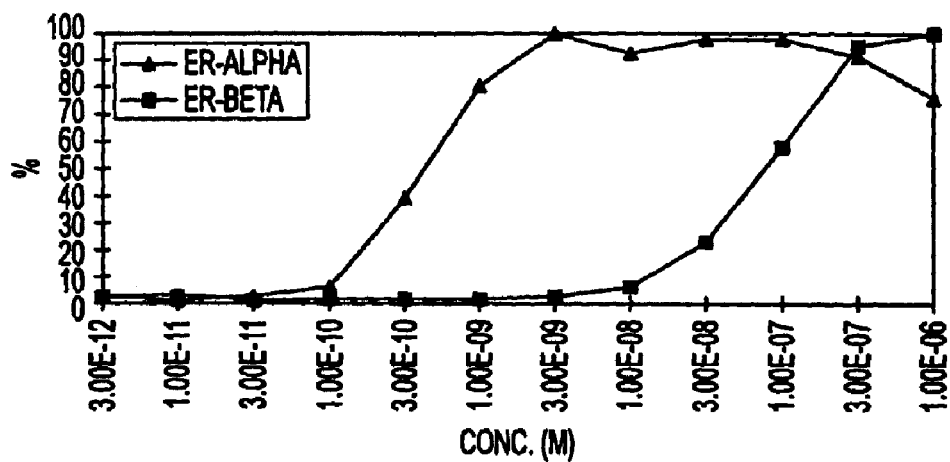

Transactivation assay sing stably transfected CHO cell lines expressing ERα or ERβ together with the rat oxytocin-luciferase estrogen-responsive reporter (see examples for details). Hormone-dependent transactivation curves were determined for 17β-estradiol (FIG. 5A) and for Org4094 (FIG. 5B). For the ER antagonist raloxifen (FIG. 5C), cells were treated with $3 \times 10^{-10}$ mol/L 17β-estradiol together with increasing concentrations of raloxifen. Maximal values of the responses were arbitrarily set at 100%.

EXAMPLES

A. Molecular Cloning of the Novel Estrogen Receptor

Two degenerate oligonucleotides containing inosines (I) were based on conserved regions of the DNA-binding domains and the ligand-binding domains of the human steroid hormone receptors.

Primer #1: 5'-GGIGA(C/T)GA(A/G)GC(A/T)TCIGGITG(C/T)CA(C/T)TA(C/T)GG-3'(SEQ ID NO:7).

Primer #2: 5'-AAGCCTGG(C/G)A(C/T)IC(G/T)(C/T)TTIGCCCAI(C/T)TIAT-3' SEQ ID NO:8).

As template, cDNA from human EBV-stimulated PBLs (peripheral blood leukocytes) was used. One microgram of total RNA was reverse transcribed in a 20 μl reaction containing 50 mM KCl, 10 mM Tris-HCl pH 8.3, 4 mM MgCl2, 1 mM dNTPs (Pharmacia), 100 pmol random hexa-nucleotides (Pharmacia), 30 Units RNAse inhibitor (Pharmacia) and 200 Units M-MLV Reverse transcriptase (Gibco BRL). Reaction mixtures were incubated at 37° C. for 30 minutes and heat-inactivated at 100° C. for 5 minutes. The cDNA obtained was used in a 100 μl PCR reaction containing 10 mM Tris-HCl pH 8.3, 50 mM KCl, 1.5 mM MgC12, 0.001% gelatin (w/v), 3% DMSO, 1 microgram of primer #1 and primer #2 and 2.5 Units of Amplitaq DNA polymerase (Perkin Elmer). PCR reactions were performed in the Perkin Elmer 9600 thermal cycler. The initial denaturation (4 minutes at 94° C.) was followed by 35 cycles with the following conditions: 30 sec. 94° C., 30 sec. 45° C., 1 minute 72° C. and after 7 minutes at 72° C. the reactions were stored at 4° C. Aliquots of these reactions were analysed on a 1.5% agarose gel. Fragments of interest were cut out of the gel, reamplified using identical PCR-conditions and purified using Qiaex II (Qiagen). Fragments were cloned in the pCRII vector and transformed into bacteria using the TA-cloning kit (Invitrogen). Plasmid DNA was isolated for nucleotide sequence analysis using the Qiagen plasmid midi protocol (Qiagen). Nucleotide sequence analysis was performed with the ALF automatic sequencer (Pharmacia) using a T7 DNA sequencing kit (Pharmacia) with vector-specific or fragment-specific primers.

One cloned fragment corresponded to a novel estrogen receptor (ER) which is closely related to the classical estrogen receptor. Part of the cloned novel estrogen receptor fragment (nucleotides 466 to 797 in SEQ ID NO:1) was amplified by PCR using oligonucleotide #3 TGTTACGAAGTGGGAATGGTGA (SEQ ID NO:9) and oligonucleotide #2 and used as a probe to screen a human testis cDNA library in λgt11 (Clontech #HL101b). Recombinant phages were plated (using Y1090 bacteria grown in LB medium supplemented with 0.2% maltose) at a density of 40.000 pfu (plaque-forming units) per 135 mm dish and replica filters (Hybond-N, Amersham) were made as described by the supplier. Filters were prehybridised in a solution containing 0.5 M phosphate buffer (pH 7.5) and 7% SDS at 65° C. for at least 30 minutes. DNA probes were purified with Qiaex II (Qiagen), $^{32}$P-labeled with a Decaprime kit (Ambion) and added to the prehybridisation solution. Filters were hybridised at 65° C. overnight and then washed in 0.5×SSC/0.1% SDS at 65° C. Two positive plaques were identified and could be shown to be identical. These clones were purified by rescreening one more time. A PCR reaction on the phage eluates with the λgt11-specific primers #4: 5'-TTGACACCAGACCAACTGGTAATG-3'(SEQ ID NO:10) and #5: 5'-GGTGGCGACGACTCCTGGAGCCCG-3'(SEQ ID NO:11) yielded a fragment of 1700 base pairs on both clones. Subsequent PCR reactions using combinations of a gene-specific primer #6: 5'-GTACACTGATTTGTAGCTGGAC-3'(SEQ ID NO:12) with the λgt11 primer #4 and gene-specific primer #7: 5'-CCATGATGATGTCCCTGACC-3'(SEQ ID NO:13) with λgt11 primer primer #5 yielded fragments of approximately 450 bp and 1000 bp, respectively, which were cloned in the pCRII vector anti used for nucleotide sequence analysis. The conditions for these PCR reactions were as described above except for the primer concentrations (200 ng of each primer) and the annealing temperature (60° C.). Since in the cDNA clone the homology with the ER is lost abruptly at a site which corresponds to the exon 7/exon 8 boundary in the ER (between nucleotides 1247 and 1248 in SEQ ID NO:1), it was suggested that this sequence corresponds to intron 7 of the novel ER gene. For verification of the nucleotide sequences of this cDNA clone, a 1200 bp fragment was generated on the cDNA clone with λgt11 primer #4 with a gene-specific primer #8 corresponding to the 3' end of exon 7: 5'-TCGCATGCCTGACGTGGGAC-3'-(SEQ ID NO:14) using the proofreading Pfu polymerase (Stratagene). This fragment was also cloned in the PCRII vector and completely sequenced and was shown to be identical to the sequences obtained earlier.

To obtain nucleotide sequences of the novel ER downstream of exon 7, a degenerate oligonucleotide based on the AF-2 region of the classical ER (#9: 5'-GGC(C/G)TCCAGCATCTCCAG(C/G)A(A/G)CAG-3'; SEQ ID NO:15) was used together with the gene-specific oligonucleotide #10: 5'-GGAAGCTGGCTCACTTGCTG-3', (SEQ ID NO:16) using testis CDNA as template (Marathon ready testis cDNA, Clontech Cat #7414-1). A specific 220 bp fragment corresponding to nucleotides 1112 to 1332 in SEQ ID NO:1 was cloned and sequenced. Nucleotides 1112 to 1247 were identical to the corresponding sequence of the cDNA clone. The sequence downstream thereof is highly homologous with the corresponding region in the classical ER. In order to obtain sequences of the novel ER downstream of the AF-2 region, RACE (rapid amplification of cDNA ends) PCR reactions were performed using the Marathon-ready testis cDNA (Clontech) as template. The initial PCR was performed using oligonucleotide #11: 5'-TCTTGTTCTGGACAGGGATG-3'(SEQ ID NO:17) in combination with the AP1 primer provided in the kit. A nested PCR was performed on an aliquot of this reaction using oligonucleotide #10 (SEQ ID NO:16) in combination with the oligo dT primer provided in the kit. Subsequently, an aliquot of this reaction was used in a nested PCR using oligonucleotide #12: 5'-GCATGGAACATCTGCTCAAC-3' (SEQ ID NO:18) in combination with the oligo dT primer. Nucleotide sequence analysis of a specific fragment that was obtained (corresponding to nucleotides 1256 to 1431 in SEQ ID NO 1) revealed a sequence encoding the carboxyterminus of the novel ER ligand-binding domain, including an F-domain and a translational stop-codon and part of the 3'untranslated sequence which is not included in SEQ ID NO:1. The deduced amino acid sequence is shown in SEQ ID NO:5.

In order to investigate the possibility that the novel estrogen receptor had additional, upstream translation-initiation codons, RACE-PCR experiments were performed using Marathon-ready testis cDNA (Clontech Cat. # 7414-1). First a PCR was performed using oligonucleotide SEQ ID NO:12 (antisense corresponding to nucleotides 416–395 in SEQ ID NO:1) and AP-1 (provided in the kit). A nested PCR was then performed using oligonucleotide having SEQ ID NO:27 (antisense corresponding to nucleotides 254–231 in SEQ ID NO:1) with AP-2 (provided in the kit). From the smear that was obtained, the region corresponding to fragments larger than 300 base pairs was cut out, purified using the GenecleanII kit (Bio101) and cloned using the TA-cloning kit (Clontech). Colonies were screened by PCR using gene-specific primers: SEQ ID NO:22 and SEQ ID NO:28. The clone containing the largest insert was sequenced. The nucleotide sequence corresponds to nucleotides 1 to 490 in SEQ ID NO:24. It is clear from this sequence that the first in-frame upstream translation initiation codon is present at position 77–79 in SEQ ID NO:24. Upstream of this translational start-codon an in-frame stop-codon is present (11–13 in SEQ ID NO:24). Consequently, the reading frame of the novel estrogen receptor is 530 amino acids (shown in SEQ ID NO:25) and has a calculated molecular mass of 59.234 kD.

To confirm the nucleotide sequences obtained by 5'RACE, human genomic clones were obtained and analysed. A human genomic library in λEMBL3 (Clontech HL1067J) was screened with a probe corresponding to nucleotides 1 to 416 in SEQ ID NO:1. A strongly hybridizing clone was plaque-purified and DNA was isolated using standard protocols (Sambrook et al, 1989). The DNA was digested with several restriction enzymes, electrophoresed on agarose gel and blotted onto Nylon filters. Hybridisation of the blot with a probe corresponding to the above-mentioned RACE fragment (nucleotides 1–490 in SEQ ID NO:24) revealed a hybridizing Sau3A fragment of approximately 800 base pairs. This fragment was cloned into the BamHI site of pGEM3Z and sequenced. The nucleotide sequence contained one base difference which is probably a PCR-induced point mutation in the RACE fragment. Nucleotide 172 was a G residue in the 5' RACE fragment, but an A residue in several independent genomic subclones.

B. Identification of Two Splice Variants of the Novel Estrogen Receptor

Rescreening of the testis CDNA library with a probe corresponding to nucleotides 918 to 1246 in SEQ ID NO:1 yielded two hybridizing clones, the 3' end of which were amplified by PCR (gene-specific primer #10: 5'-GGAAGCTGGCTCACTTGCTG-3'(SEQ ID NO:16) together with primer #4, SEQ ID NO:10), cloned and sequenced. One clone was shown to contain an alternative exon 8 (exon 8B) of the novel ER. In SEQ ID NO:2 the protein encoding part and the stop-codon of this splice variant are presented. As a consequence of the introduction of this exon through an alternative splicing reaction, the reading frame encoding the novel ER is immediately terminated, thereby creating a truncation of the carboxyterminus of the novel ER (SEQ ID NO:6).

Screening of a human thymus cDNA library (Clontech HL1074a) with the probe corresponding to nucleotides 918 to 1246 in SEQ ID NO:1, revealed another splice variant. The 3' end of one hybridizing clone was amplified using primer #10 (SEQ ID NO:16) with the λgt10-specific primer #13 5'-AGCAAGTTCAGCCTGTTAAGT-3'(SEQ ID NO:19), cloned and sequenced. The obtained nucleotide sequence upstream of the exon 7/exon 8 boundary was identical to the clones identified earlier. However, an alternative exon 8 (exon 8C) was present at the 3'end encoding two C-terminal amino acids followed by a stop-codon. The nucleotide sequence of the protein-encoding part of this splice variant is shown in SEQ ID NO:20, the corresponding protein sequence is SEQ ID NO:21.

These two variants of the novel estrogen receptor do not contain the AF-2 region and therefore probably lack the ability to modulate transcription of target genes in a ligand-dependent fashion. However, the variants potentially could interfere with the functioning of the wild-type classical ER and/or the wild-type novel ER, either by heterodimerization or by occupying estrogen response elements or by interactions with other transcription factors. A mutant of the classical ER (ERI-530) has been described which closely resembles the two variants of the novel estrogen receptor described above. ERl-530 has been shown to behave as a dominant-negative receptor i.e. it can modulate the intracellular activity of the wild type ER (Ince et al, J. Biol. Chem. 268, 14026–14032, 1993).

C. Northern Blot Analysis

Human multiple tissue Northern blots (MTN-blots) were purchased from Clontech and prehybridized for at least 1 hour at 65° C. in 0.5 M phosphate buffer pH 7.5 with 7% SDS. The DNA fragment that was used as a probe (corresponding to nucleotides 466 to 797 in SEQ ID NO:1) was $^{32}$P-labeled using a labelling kit (Ambion), denatured by boiling and added to the prehybridisation solution. Washing conditions were: 3×SSC at room temperature, followed by 3×SSC at 65° C., and finally 1×SSC at 65° C. The filters were than exposed to X-ray films for one week. Two transcripts of approximately 8 kb and 10 kb were detected in thymus, spleen, ovary and testis. In addition, a 1.3 kb transcript was detected in testis.

D. RT-PCR Analysis of Expression of ERα and ERβ in Cell Lines

Figure 4:
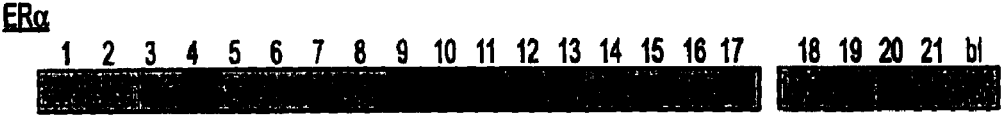
Figure 4:
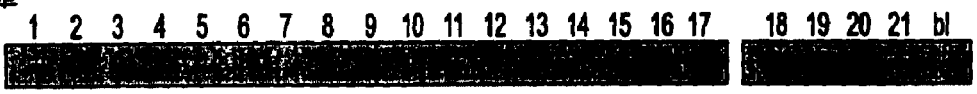

RNA was isolated from a number of human and animal cell lines using RNAzol B (Cinna/Biotecx). cDNA was made using 2.5 microgram of total RNA using the Superscript II kit (BRL) following the manufacturer's instructions. A portion of the cDNA was used for specific PCR amplifications of fragments corresponding either to mRNA encoding the ER or to the novel estrogen receptor. (It should be emphasized that the primers used are based on human and rat sequences, whereas some of the cell lines were not rat or human, see legend of FIG. 4). Primers used were for ERα: sense 5'-GATGGGCTTACTGACCAACC-3' (SEQ ID NO:29) and antisense 5'-AGATGCTCCATGCC TTG-3' (SEQ ID NO:30) generating a 548 base pair fragment corresponding to part of the LBD. For ERRβ: sense 5'-TTCACCGAGGCCTCCATGATG-3'(SEQ ID NO:31) and antisense 5'-CAGATGTTCCATGCCCTTGTT-3'(SEQ ID NO:32) generating a 565 base pair fragment corresponding to part of the LBD. The PCR samples were analysed on agarose which were blotted onto Nylon® membranes. These blots were hybridised with $^{32}$P-labeled PCR fragments generated with the above-mentioned primers on ERα and ERβ plasmid DNA using standard experimental procedures (Sambrook et al., 1989).

E. Ligand-Dependent Transcription Activation by the Novel Estrogen Receptor Protein Cell culture Chinese Hamster Ovary (CHO K1) cells were obtained from ATCC (CCL61) and maintained at 37° C. in a humidified atmosphere (5% $CO_2$) as a monolayer culture in fenolred-free M505 medium. The latter medium consists of a mixture (1:1) of Dulbecco's Modified Eagle's Medium (DMEM, Gibco 074–200) and Nutrient Medium F12 (Ham's F12, Gibco 074–1700) supplemented with 2.5 mg/ml sodium carbonate (Baker), 55 µg/ml sodium pyruvate (Fluka), 2.3 µg/ml β-mercaptoethanol (Baker), 1.2 µg/ml ethanolamine (Baker), 360 µg/ml L-glutamine (Merck), 0.45 µg/ml sodium selenite (Fluka), 62.5 µg/ml penicillin (Mycopharm), 62.5 µg/ml streptomycin (Serva), and 5% charcoal-treated bovine calf serum (Hyclone).

Recombinant vectors

The ERβ-encoding sequence as presented in SEQ ID NO:1 was amplified by PCR using oligonucleotides 5'-CTTGGATCCATAGCCCTGCTGTG ATGAATTACAG-3'(SEQ ID NO:22 underlined is the translation initiation codon) in combination with 5'-GATGGATCCTCACCTCAGGGCCAGGCG TCACTG-3'(SEQ ID NO:23) (underlined is the translation stop-codon, antisense). The resulting BamHl fragment (approximately 1450 base pairs) were then cloned in the mammalian cell expression vector pNGV1 (Genbank accession No. X99274).

An expression construct encoding the ERβ reading frame as presented in SEQ ID NO:24 was made by replacing a BamHl-Mscl fragment (nucleotides 1–81 in SEQ ID NO:1) by a BamHl-Mscl fragment corresponding to nucleotides 77–316 in SEQ ID NO:24. The latter fragment was made by PCR with SEQ ID NO:26 in combination with SEQ ID NO:28 using the above mentioned 5' RACE fragment.

The reporter vector was based on the rat oxytocin gene regulatory region (position -363/+16 as a HindIII/MboI fragment; R. Ivell, and D. Richter, Proc. Natl. Acad. Sci. USA 81, 2006–2010, 1984) linked to the firefly luciferase encoding sequence; the regulatory region of the oxytocin gene was shown to possess functional estrogen hormone response elements in vitro for both the rat (R. Adan et al, Biochem. Biophys. Res. Comm. 175, 117–122, 1991) and the human (S. Richard, and H. Zingg, J. Biol. Chem. 265, 6098–6103, 1990).

Transient transfection $1 \times 10^5$ CHO cells were seeded in 6-wells Nunclon tissue culture plates and DNA was introduced by use of lipofectin (Gibco BRL). Hereto, the DNA (1 µg of both receptor and reporter vector in 250 µL Optimem, Gibco BRL) was mixed with an equal volume of lipofectin reagent (7 µL in 250 µL Optimem, Gibco) and allowed to stand at room temperature for 15 min. After washing the cells twice with serum-free medium (M505) new medium (500 µL Optimem, Gibco) was added to the cells followed by the dropwise addition of the DNA-lipofectin mixture. After incubation for a 5 hour period at 37° C. cells were washed twice with fenolred-free M505+5% charcoal-treated bovine calf serum and incubated overnight at 37° C. After 24 hours hormones were added to the medium ($10^{-7}$ mol/L). Cell extracts were made 48 hours post-transfection by the addition of 200 µL lysisbuffer (0.1 M phosphate buffer pH7.8, 0.2% Triton X-100). After incubation for 5 min at 37° C. the cell suspension was centrifuged (Eppendorf centrifuge, 5 min) and 20 µL sample was added to 50 µL luciferase assay reagent (Promega). Light emission was measured in a luminometer (Berthold Biolumat) for 10 sec at 562 nm.

Stable transfection of the novel estrogen receptor.

The expression plasmid encoding full-length ERβ1-530 (see above) was stably transfected in CHO K1 cells as previously described (Theunissen et al., J. Biol. Chem. 268, 9035–9040, 1993). Single cell clones that were obtained this way were screened by transient transfection of the reporter plasmid (rat oxytocin-luciferase) as described above. Selected clones were used for a second stable transfection of the rat oxytocin-luciferase reporter plasmid together with the plasmid pDR2A which contains a hygromycine resistance gene for selection. Single cell clones obtained were tested for a response to 17β-estradiol. Subsequently, a selected single cell clone was used for transactivation studies. Briefly, cells were seeded in 96-wells at ($1.6 \times 10^4$ cells per well). After 24 hours different concentrations of hormone were diluted in medium and added to the wells. For antagonistic experiments, $2 \times 10^{-10}$ M. 17β-estradiol was added to each well and different concentrations of antagonists were added. Cells were washed once with PBS after a 24 hour incubation and then lysed by the addition of 40 microliter lysis buffer (see above). Luciferase reagent was added (50 microliter) to each well and light emission was measured using the Topcount (Packard).

Results

Figure 2:
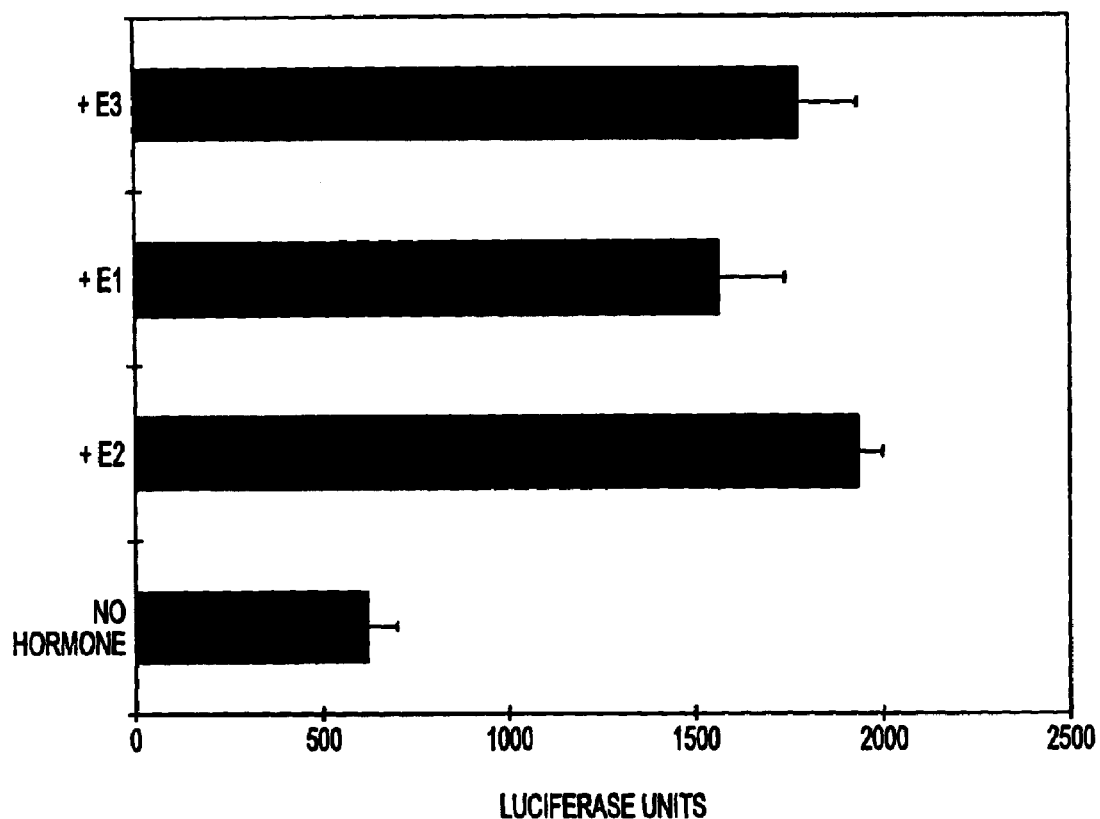
Figure 3:
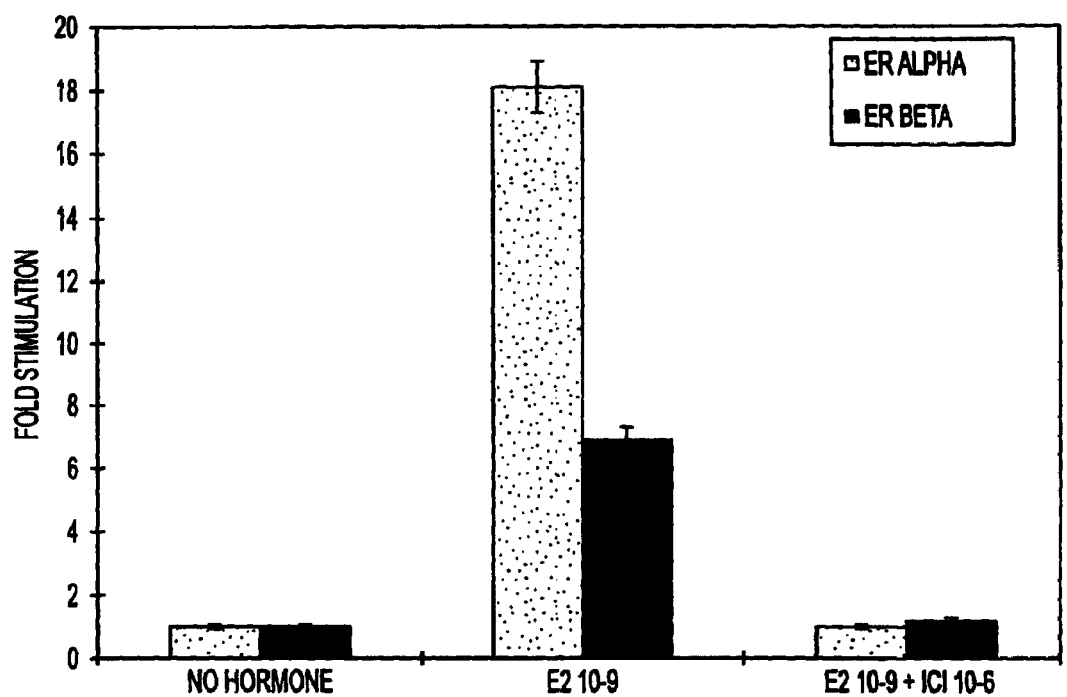

A comparison of the two expression constructs (SEQ ID NO:1 and SEQ ID NO:24) in transient transfections in CHO cells showed identical transactivation in response to a number of agonists and antagonists. CHO cells transiently transfected with ERβ expression vector and a reporter plasmid showed a 3 to 4 fold increase in luciferase activity in response to 17β-estradiol as compared to untreated cells (see FIG. 2). A similar transactivation was obtained upon treatment with estriol and estrone. The results indicate not only that the novel ER (ERβ) can bind estrogen hormones but also that the ligand-activated receptor can bind to the estrogen-response elements (EREs) within the rat oxytocin promoter and activate transcription of the luciferase reporter gene. FIG. 3 shows that in an independent similar experiment $10^{-9}$ mol/L 17β-estradiol gave an 18-fold stimulation with ERα and a 7-fold stimulation with ERA. In addition, the antiestrogen ICI-164384 was shown to be an antagonist for both ERα and ERβ when activated with 17β-estradiol, whereas the antagonist alone had no effect. In this experiment 0.25 µg β-galactosidase vector was co-transfected in order to normalize for differences in transfection efficiency.

Figure 5C:
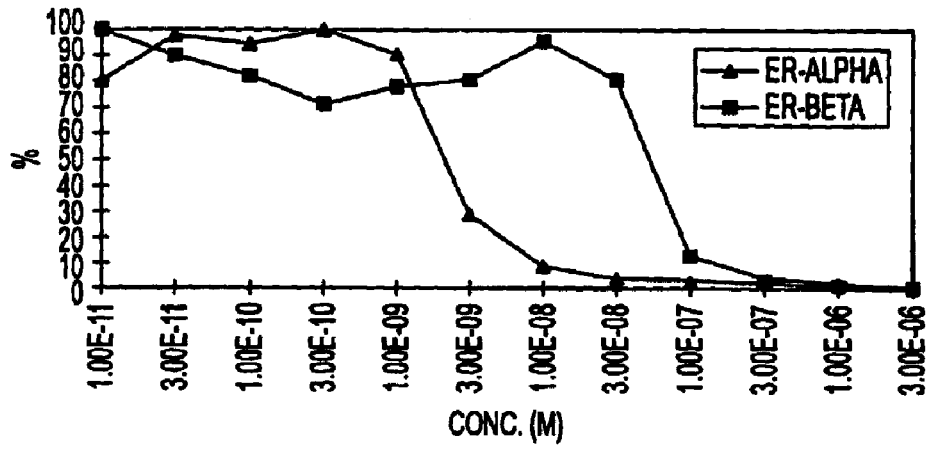

Transactivation studies performed on stably transfected ERα and ERβ cell lines gave similar absolute luciferase values. The curves for 17β-estradiol are very similar and show that half-maximal transactivation is reached with lower concentrations of hormone on ERα as compared to ERβ (FIGS. 5A–5C). For Org4094 this is also the case however, the effect observed is much more pronounced. The curves for raloxifen show that the potency of this antagonist to block transactivation on ERα is greater compared to its potency to block ERβ transactivation.

What is claimed is:

1. An isolated DNA encoding a human estrogen receptor protein having an N-terminal domain, a DNA-binding domain and a ligand-binding domain, wherein said protein comprises an amino acid sequence selected from the group consisting of the amino acid sequence set forth in SEQ ID NO:5, the amino acid sequence set forth in SEQ ID NO:6, the amino acid sequence set forth in SEQ ID NO:21 and the amino acid sequence set forth in SEQ ID NO:25.

2. An isolated DNA encoding a human estrogen receptor protein having an N-terminal domain, a DNA-binding domain and a ligand-binding domain, wherein said DNA comprises a nucleic acid sequence selected from the group consisting of the nucleotide sequence set forth in SEQ ID NO:1, the nucleotide sequence set forth in SEQ ID NO:2, the nucleotide sequence set forth in SEQ ID NO:20 and the nucleotide sequence set forth in SEQ ID NO:24.

3. A recombinant expression vector comprising the DNA according to claim 1.

4. A cell transfected with the expression vector according to claim 3.

5. The cell according to claim 4, which is a stable transfected cell line that expresses the human estrogen receptor protein.

6. A recombinant expression vector comprising the DNA according to claim 2.

7. A cell transfected with the expression vector according to claim 6.

8. The cell according to claim 7, which is a stable transfected cell line that expresses the human estrogen receptor protein.

* * * * *

SEQUENCE LISTING

<160> NUMBER OF SEQ ID NOS: 32

<210> SEQ ID NO 1
<211> LENGTH: 1434
<212> TYPE: DNA
<213> ORGANISM: Homo sapiens

<400> SEQUENCE: 1

| | | | | | |
|---|---|---|---|---|---|
| atgaattaca | gcattcccag | caatgtcact | aacttggaag | gtgggcctgg | tcggcagacc | 60 |
| acaagcccaa | atgtgttgtg | gccaacacct | gggcaccttt | ctcctttagt | ggtccatcgc | 120 |
| cagttatcac | atctgtatgc | ggaacctcaa | aagagtccct | ggtgtgaagc | aagatcgcta | 180 |
| gaacacacct | tacctgtaaa | cagagagaca | ctgaaaagga | aggttagtgg | gaaccgttgc | 240 |
| gccagccctg | ttactggtcc | aggttcaaag | agggatgctc | acttctgcgc | tgtctgcagc | 300 |
| gattacgcat | cgggatatca | ctatggagtc | tggtcgtgtg | aaggatgtaa | ggcctttttt | 360 |
| aaaagaagca | ttcaaggaca | taatgattat | atttgtccag | ctacaaatca | gtgtacaatc | 420 |
| gataaaaacc | ggcgcaagag | ctgccaggcc | tgccgacttc | ggaagtgtta | cgaagtggga | 480 |
| atggtgaagt | gtggctcccg | gagagagaga | tgtgggtacc | gccttgtgcg | gagacagaga | 540 |
| agtgccgacg | agcagctgca | ctgtgccggc | aaggccaaga | agagtggcgg | ccacgcgccc | 600 |
| cgagtgcggg | agctgctgct | ggacgccctg | agccccgagc | agctagtgct | caccctcctg | 660 |
| gaggctgagc | cgcccatgt  | gctgatcagc | cgccccagtg | cgcccttcac | cgaggcctcc | 720 |
| atgatgatgt | ccctgaccaa | gttggccgac | aaggagttgg | tacacatgat | cagctgggcc | 780 |
| aagaagattc | ccggctttgt | ggagctcagc | ctgttcgacc | aagtgcggct | cttggagagc | 840 |
| tgttggatgg | aggtgttaat | gatggggctg | atgtggcgct | caattgacca | ccccggcaag | 900 |
| ctcatctttg | ctccagatct | tgttctggac | agggatgagg | ggaaatgcgt | agaaggaatt | 960 |
| ctggaaatct | ttgacatgct | cctggcaact | acttcaaggt | ttcgagagtt | aaaactccaa | 1020 |
| cacaaagaat | atctctgtgt | caaggccatg | atcctgctca | attccagtat | gtaccctctg | 1080 |
| gtcacagcga | cccaggatgc | tgacagcagc | cggaagctgg | ctcacttgct | gaacgccgtg | 1140 |
| accgatgctt | tggtttgggt | gattgccaag | agcggcatct | cctcccagca | gcaatccatg | 1200 |
| cgcctggcta | acctcctgat | gctcctgtcc | cacgtcaggc | atgcgagtaa | caagggcatg | 1260 |
| gaacatctgc | tcaacatgaa | gtgcaaaaat | gtggtcccag | tgtatgacct | gctgctggag | 1320 |
| atgctgaatg | cccacgtgct | cgcgggtgc  | aagtcctcca | tcacgggtc  | cgagtgcagc | 1380 |
| ccggcagagg | acagtaaaag | caaagagggc | tcccagaacc | cacagtctca | gtga | 1434 |

<210> SEQ ID NO 2
<211> LENGTH: 1251
<212> TYPE: DNA
<213> ORGANISM: Homo sapiens

<400> SEQUENCE: 2

| | | | | | |
|---|---|---|---|---|---|
| atgaattaca | gcattcccag | caatgtcact | aacttggaag | gtgggcctgg | tcggcagacc | 60 |
| acaagcccaa | atgtgttgtg | gccaacacct | gggcaccttt | ctcctttagt | ggtccatcgc | 120 |
| cagttatcac | atctgtatgc | ggaacctcaa | aagagtccct | ggtgtgaagc | aagatcgcta | 180 |
| gaacacacct | tacctgtaaa | cagagagaca | ctgaaaagga | aggttagtgg | gaaccgttgc | 240 |
| gccagccctg | ttactggtcc | aggttcaaag | agggatgctc | acttctgcgc | tgtctgcagc | 300 |
| gattacgcat | cgggatatca | ctatggagtc | tggtcgtgtg | aaggatgtaa | ggcctttttt | 360 |

```
aaaagaagca ttcaaggaca taatgattat atttgtccag ctacaaatca gtgtacaatc   420
gataaaaacc ggcgcaagag ctgccaggcc tgccgacttc ggaagtgtta cgaagtggga   480
atggtgaagt gtggctcccg gagagagaga tgtgggtacc gccttgtgcg agacagaga   540 agtgccgacg agcagctgca ctgtgccggc aaggccaaga gaagtggcgg ccacgcgccc   600
cgagtgcggg agctgctgct ggacgccctg agccccgagc agctagtgct cacccteetg   660 gaggctgagc cgccccatgt gctgatcagc cgccccagtg cgcccttcac cgaggcctcc   720
atgatgatgt ccctgaccaa gttggccgac aaggagttgg tacacatgat cagctgggcc   780
aagaagattc ccggctttgt ggagctcagc ctgttcgacc aagtgcggct cttggagagc   840
tgttggatgg aggtgttaat gatggggctg atgtggcgct caattgacca ccccggcaag   900
ctcatctttg ctccagatct tgttctggac agggatgagg ggaaatgcgt agaaggaatt   960
ctggaaatct ttgacatgct cctggcaact acttcaaggt ttcgagagtt aaaactccaa   1020
cacaaagaat atctctgtgt caaggccatg atcctgctca attccagtat gtaccctctg   1080
gtcacagcga cccaggatgc tgacagcagc cggaagctgg ctcacttgct gaacgccgtg   1140
accgatgctt tggtttgggt gattgccaag agcggcatct cctcccagca gcaatccatg   1200
cgcctggcta acctcctgat gctcctgtcc cacgtcaggc atgcgaggtg a            1251
```

<210> SEQ ID NO 3
<211> LENGTH: 66
<212> TYPE: PRT
<213> ORGANISM: Homo sapiens

<400> SEQUENCE: 3

```
Cys Ala Val Cys Ser Asp Tyr Ala Ser Gly Tyr His Tyr Gly Val Trp
1               5                   10                  15

Ser Cys Glu Gly Cys Lys Ala Phe Phe Lys Arg Ser Ile Gln Gly His
            20                  25                  30

Asn Asp Tyr Ile Cys Pro Ala Thr Asn Gln Cys Thr Ile Asp Lys Asn
        35                  40                  45

Arg Arg Lys Ser Cys Gln Ala Cys Arg Leu Arg Lys Cys Tyr Glu Val
    50                  55                  60

Gly Met
65
```

<210> SEQ ID NO 4
<211> LENGTH: 233
<212> TYPE: PRT
<213> ORGANISM: Homo sapiens

<400> SEQUENCE: 4

```
Leu Val Leu Thr Leu Leu Glu Ala Glu Pro Pro His Val Leu Ile Ser
1               5                   10                  15

Arg Pro Ser Ala Pro Phe Thr Glu Ala Ser Met Met Met Ser Leu Thr
            20                  25                  30

Lys Leu Ala Asp Lys Glu Leu Val His Met Ile Ser Trp Ala Lys Lys
        35                  40                  45

Ile Pro Gly Phe Val Glu Leu Ser Leu Phe Asp Gln Val Arg Leu Leu
    50                  55                  60

Glu Ser Cys Trp Met Glu Val Leu Met Met Gly Leu Met Trp Arg Ser
65                  70                  75                  80

Ile Asp His Pro Gly Lys Leu Ile Phe Ala Pro Asp Leu Val Leu Asp
            85                  90                  95
```

```
Arg Asp Glu Gly Lys Cys Val Glu Gly Ile Leu Glu Ile Phe Asp Met
            100                 105                 110

Leu Leu Ala Thr Thr Ser Arg Phe Arg Glu Leu Lys Leu Gln His Lys
        115                 120                 125

Glu Tyr Leu Cys Val Lys Ala Met Ile Leu Leu Asn Ser Ser Met Tyr
    130                 135                 140

Pro Leu Val Thr Ala Thr Gln Asp Ala Asp Ser Ser Arg Lys Leu Ala
145                 150                 155                 160

His Leu Leu Asn Ala Val Thr Asp Ala Leu Val Trp Val Ile Ala Lys
                165                 170                 175

Ser Gly Ile Ser Ser Gln Gln Ser Met Arg Leu Ala Asn Leu Leu
                180                 185                 190

Met Leu Leu Ser His Val Arg His Ala Ser Asn Lys Gly Met Glu His
        195                 200                 205

Leu Leu Asn Met Lys Cys Lys Asn Val Val Pro Val Tyr Asp Leu Leu
        210                 215                 220

Leu Glu Met Leu Asn Ala His Val Leu
225                 230

<210> SEQ ID NO 5
<211> LENGTH: 477
<212> TYPE: PRT
<213> ORGANISM: Homo sapiens

<400> SEQUENCE: 5

Met Asn Tyr Ser Ile Pro Ser Asn Val Thr Asn Leu Glu Gly Gly Pro
1               5                   10                  15

Gly Arg Gln Thr Thr Ser Pro Asn Val Leu Trp Pro Thr Pro Gly His
            20                  25                  30

Leu Ser Pro Leu Val Val His Arg Gln Leu Ser His Leu Tyr Ala Glu
        35                  40                  45

Pro Gln Lys Ser Pro Trp Cys Glu Ala Arg Ser Leu Glu His Thr Leu
    50                  55                  60

Pro Val Asn Arg Glu Thr Leu Lys Arg Lys Val Ser Gly Asn Arg Cys
65                  70                  75                  80

Ala Ser Pro Val Thr Gly Pro Gly Ser Lys Arg Asp Ala His Phe Cys
                85                  90                  95

Ala Val Cys Ser Asp Tyr Ala Ser Gly Tyr His Tyr Gly Val Trp Ser
            100                 105                 110

Cys Glu Gly Cys Lys Ala Phe Phe Lys Arg Ser Ile Gln Gly His Asn
        115                 120                 125

Asp Tyr Ile Cys Pro Ala Thr Asn Gln Cys Thr Ile Asp Lys Asn Arg
    130                 135                 140

Arg Lys Ser Cys Gln Ala Cys Arg Leu Arg Lys Cys Tyr Glu Val Gly
145                 150                 155                 160

Met Val Lys Cys Gly Ser Arg Arg Glu Arg Cys Gly Tyr Arg Leu Val
                165                 170                 175

Arg Arg Gln Arg Ser Ala Asp Glu Gln Leu His Cys Ala Gly Lys Ala
            180                 185                 190

Lys Arg Ser Gly Gly His Ala Pro Arg Val Arg Glu Leu Leu Leu Asp
        195                 200                 205

Ala Leu Ser Pro Glu Gln Leu Val Leu Thr Leu Leu Glu Ala Glu Pro
    210                 215                 220

Pro His Val Leu Ile Ser Arg Pro Ser Ala Pro Phe Thr Glu Ala Ser
```

```
                225                 230                 235                 240
Met Met Met Ser Leu Thr Lys Leu Ala Asp Lys Glu Leu Val His Met
                245                 250                 255

Ile Ser Trp Ala Lys Lys Ile Pro Gly Phe Val Glu Leu Ser Leu Phe
                260                 265                 270

Asp Gln Val Arg Leu Leu Glu Ser Cys Trp Met Glu Val Leu Met Met
                275                 280                 285

Gly Leu Met Trp Arg Ser Ile Asp His Pro Gly Lys Leu Ile Phe Ala
                290                 295                 300

Pro Asp Leu Val Leu Asp Arg Asp Glu Gly Lys Cys Val Glu Gly Ile
305                 310                 315                 320

Leu Glu Ile Phe Asp Met Leu Leu Ala Thr Thr Ser Arg Phe Arg Glu
                325                 330                 335

Leu Lys Leu Gln His Lys Glu Tyr Leu Cys Val Lys Ala Met Ile Leu
                340                 345                 350

Leu Asn Ser Ser Met Tyr Pro Leu Val Thr Ala Thr Gln Asp Ala Asp
                355                 360                 365

Ser Ser Arg Lys Leu Ala His Leu Leu Asn Ala Val Thr Asp Ala Leu
                370                 375                 380

Val Trp Val Ile Ala Lys Ser Gly Ile Ser Ser Gln Gln Gln Ser Met
385                 390                 395                 400

Arg Leu Ala Asn Leu Leu Met Leu Leu Ser His Val Arg His Ala Ser
                405                 410                 415

Asn Lys Gly Met Glu His Leu Leu Asn Met Lys Cys Lys Asn Val Val
                420                 425                 430

Pro Val Tyr Asp Leu Leu Leu Glu Met Leu Asn Ala His Val Leu Arg
                435                 440                 445

Gly Cys Lys Ser Ser Ile Thr Gly Ser Glu Cys Ser Pro Ala Glu Asp
                450                 455                 460

Ser Lys Ser Lys Glu Gly Ser Gln Asn Pro Gln Ser Gln
465                 470                 475

<210> SEQ ID NO 6
<211> LENGTH: 416
<212> TYPE: PRT
<213> ORGANISM: Homo sapiens

<400> SEQUENCE: 6

Met Asn Tyr Ser Ile Pro Ser Asn Val Thr Asn Leu Glu Gly Gly Pro
1               5                   10                  15

Gly Arg Gln Thr Thr Ser Pro Asn Val Leu Trp Pro Thr Pro Gly His
                20                  25                  30

Leu Ser Pro Leu Val Val His Arg Gln Leu Ser His Leu Tyr Ala Glu
                35                  40                  45

Pro Gln Lys Ser Pro Trp Cys Glu Ala Arg Ser Leu Glu His Thr Leu
                50                  55                  60

Pro Val Asn Arg Glu Thr Leu Lys Arg Lys Val Ser Gly Asn Arg Cys
65                  70                  75                  80

Ala Ser Pro Val Thr Gly Pro Gly Ser Lys Arg Asp Ala His Phe Cys
                85                  90                  95

Ala Val Cys Ser Asp Tyr Ala Ser Gly Tyr His Tyr Gly Val Trp Ser
                100                 105                 110

Cys Glu Gly Cys Lys Ala Phe Phe Lys Arg Ser Ile Gln Gly His Asn
                115                 120                 125
```

-continued

```
Asp Tyr Ile Cys Pro Ala Thr Asn Gln Cys Thr Ile Asp Lys Asn Arg
        130                 135                 140

Arg Lys Ser Cys Gln Ala Cys Arg Leu Arg Lys Cys Tyr Glu Val Gly
145                 150                 155                 160

Met Val Lys Cys Gly Ser Arg Arg Glu Arg Cys Gly Tyr Arg Leu Val
                165                 170                 175

Arg Arg Gln Arg Ser Ala Asp Glu Gln Leu His Cys Ala Gly Lys Ala
            180                 185                 190

Lys Arg Ser Gly Gly His Ala Pro Arg Val Arg Glu Leu Leu Leu Asp
        195                 200                 205

Ala Leu Ser Pro Glu Gln Leu Val Leu Thr Leu Leu Glu Ala Glu Pro
    210                 215                 220

Pro His Val Leu Ile Ser Arg Pro Ser Ala Pro Phe Thr Glu Ala Ser
225                 230                 235                 240

Met Met Met Ser Leu Thr Lys Leu Ala Asp Lys Glu Leu Val His Met
                245                 250                 255

Ile Ser Trp Ala Lys Lys Ile Pro Gly Phe Val Glu Leu Ser Leu Phe
            260                 265                 270

Asp Gln Val Arg Leu Leu Glu Ser Cys Trp Met Glu Val Leu Met Met
        275                 280                 285

Gly Leu Met Trp Arg Ser Ile Asp His Pro Gly Lys Leu Ile Phe Ala
    290                 295                 300

Pro Asp Leu Val Leu Asp Arg Asp Glu Gly Lys Cys Val Glu Gly Ile
305                 310                 315                 320

Leu Glu Ile Phe Asp Met Leu Leu Ala Thr Thr Ser Arg Phe Arg Glu
                325                 330                 335

Leu Lys Leu Gln His Lys Glu Tyr Leu Cys Val Lys Ala Met Ile Leu
            340                 345                 350

Leu Asn Ser Ser Met Tyr Pro Leu Val Thr Ala Thr Gln Asp Ala Asp
        355                 360                 365

Ser Ser Arg Lys Leu Ala His Leu Leu Asn Ala Val Thr Asp Ala Leu
    370                 375                 380

Val Trp Val Ile Ala Lys Ser Gly Ile Ser Ser Gln Gln Gln Ser Met
385                 390                 395                 400

Arg Leu Ala Asn Leu Leu Met Leu Leu Ser His Val Arg His Ala Arg
                405                 410                 415
```

<210> SEQ ID NO 7
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: n is inosine

<400> SEQUENCE: 7
ggngaygarg cwtcnggntg ycaytaygg                29

<210> SEQ ID NO 8
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: n is inosine

<400> SEQUENCE: 8
aacggtggsa ynckyttngc ccanytnat                                    29

<210> SEQ ID NO 9
<211> LENGTH: 22
<212> TYPE: DNA
<213> ORGANISM: Homo sapiens

<400> SEQUENCE: 9
tgttacgaag tgggaatggt ga                                           22

<210> SEQ ID NO 10
<211> LENGTH: 24
<212> TYPE: DNA
<213> ORGANISM: Homo sapiens

<400> SEQUENCE: 10
ttgacaccag accaactggt aatg                                         24

<210> SEQ ID NO 11
<211> LENGTH: 24
<212> TYPE: DNA
<213> ORGANISM: Homo sapiens

<400> SEQUENCE: 11
ggtggcgacg actcctggag cccg                                         24

<210> SEQ ID NO 12
<211> LENGTH: 22
<212> TYPE: DNA
<213> ORGANISM: Homo sapiens

<400> SEQUENCE: 12
gtacactgat ttgtagctgg ac                                           22

<210> SEQ ID NO 13
<211> LENGTH: 20
<212> TYPE: DNA
<213> ORGANISM: Homo sapiens

<400> SEQUENCE: 13
ccatgatgat gtccctgacc                                              20

<210> SEQ ID NO 14
<211> LENGTH: 20
<212> TYPE: DNA
<213> ORGANISM: Homo sapiens

<400> SEQUENCE: 14
tcgcatgcct gacgtgggac                                              20

<210> SEQ ID NO 15
<211> LENGTH: 24
<212> TYPE: DNA
<213> ORGANISM: Homo sapiens

<400> SEQUENCE: 15
ggcstccagc atctccagsa rcag                                         24

<210> SEQ ID NO 16
<211> LENGTH: 20
<212> TYPE: DNA
<213> ORGANISM: Homo sapiens -continued

<400> SEQUENCE: 16
ggaagctggc tcacttgctg                                                   20

<210> SEQ ID NO 17
<211> LENGTH: 20
<212> TYPE: DNA
<213> ORGANISM: Homo sapiens

<400> SEQUENCE: 17
tcttgttctg gacagggatg                                                   20

<210> SEQ ID NO 18
<211> LENGTH: 20
<212> TYPE: DNA
<213> ORGANISM: Homo sapiens

<400> SEQUENCE: 18
gcatggaaca tctgctcaac                                                   20

<210> SEQ ID NO 19
<211> LENGTH: 21
<212> TYPE: DNA
<213> ORGANISM: Homo sapiens

<400> SEQUENCE: 19
agcaagttca gcctgttaag t                                                 21

<210> SEQ ID NO 20
<211> LENGTH: 1257
<212> TYPE: DNA
<213> ORGANISM: Homo sapiens

<400> SEQUENCE: 20
atgaattaca gcattcccag caatgtcact aacttggaag gtgggcctgg tcggcagacc         60
acaagcccaa atgtgttgtg ccaacacct gggcaccttt ctcctttagt ggtccatcgc        120
cagttatcac atctgtatgc ggaacctcaa aagagtccct ggtgtgaagc aagatcgcta       180
gaacacacct tacctgtaaa cagagagaca ctgaaaagga aggttagtgg gaaccgttgc       240
gccagccctg ttactggtcc aggttcaaag agggatgctc acttctgcgc tgtctgcagc       300
gattacgcat cgggatatca ctatggagtc tggtcgtgtg aaggatgtaa ggccttttt       360 aaaagaagca ttcaaggaca taatgattat atttgtccag ctacaaatca gtgtacaatc       420
gataaaaacc ggcgcaagag ctgccaggcc tgccgacttc ggaagtgtta cgaagtggga       480
atggtgaagt gtggctcccg gagagagaga tgtgggtacc gccttgtgcg gagacagaga       540
agtgccgacg agcagctgca ctgtgccggc aaggccaaga gaagtggcgg ccacgcgccc       600
cgagtgcggg agctgctgct ggacgccctg agccccgagc agctagtgct cacccctcctg      660 gaggctgagc cgccccatgt gctgatcagc cgccccagtg cgcccttcac cgaggcctcc       720
atgatgatgt ccctgaccaa gttggccgac aaggagttgg tacacatgat cagctgggcc       780
aagaagattc ccggctttgt ggagctcagc ctgttcgacc aagtgcggct cttggagagc       840
tgttggatgg aggtgttaat gatggggctg atgtggcgct caattgacca ccccggcaag       900
ctcatctttg ctccagatct tgttctggac agggatgagg ggaaatgcgt agaaggaatt       960
ctggaaatct tgacatgct cctggcaact acttcaaggt ttcgagagtt aaaactccaa      1020
cacaaagaat atctctgtgt caaggccatg atcctgctca attccagtat gtaccctctg      1080
gtcacagcga cccaggatgc tgacagcagc cggaagctgg ctcacttgct gaacgccgtg      1140

-continued

```
accgatgctt tggtttgggt gattgccaag agcggcatct cctcccagca gcaatccatg    1200
cgcctggcta acctcctgat gctcctgtcc cacgtcaggc atgcgaggtc tgcctga       1257
```

<210> SEQ ID NO 21
<211> LENGTH: 418
<212> TYPE: PRT
<213> ORGANISM: Homo sapiens

<400> SEQUENCE: 21

```
Met Asn Tyr Ser Ile Pro Ser Asn Val Thr Asn Leu Glu Gly Gly Pro
1               5                   10                  15

Gly Arg Gln Thr Thr Ser Pro Asn Val Leu Trp Pro Thr Pro Gly His
            20                  25                  30

Leu Ser Pro Leu Val Val His Arg Gln Leu Ser His Leu Tyr Ala Glu
        35                  40                  45

Pro Gln Lys Ser Pro Trp Cys Glu Ala Arg Ser Leu Glu His Thr Leu
    50                  55                  60

Pro Val Asn Arg Glu Thr Leu Lys Arg Lys Val Ser Gly Asn Arg Cys
65                  70                  75                  80

Ala Ser Pro Val Thr Gly Pro Gly Ser Lys Arg Asp Ala His Phe Cys
                85                  90                  95

Ala Val Cys Ser Asp Tyr Ala Ser Gly Tyr His Tyr Gly Val Trp Ser
            100                 105                 110

Cys Glu Gly Cys Lys Ala Phe Phe Lys Arg Ser Ile Gln Gly His Asn
        115                 120                 125

Asp Tyr Ile Cys Pro Ala Thr Asn Gln Cys Thr Ile Asp Lys Asn Arg
    130                 135                 140

Arg Lys Ser Cys Gln Ala Cys Arg Leu Arg Lys Cys Tyr Glu Val Gly
145                 150                 155                 160

Met Val Lys Cys Gly Ser Arg Arg Glu Arg Cys Gly Tyr Arg Leu Val
                165                 170                 175

Arg Arg Gln Arg Ser Ala Asp Glu Gln Leu His Cys Ala Gly Lys Ala
            180                 185                 190

Lys Arg Ser Gly Gly His Ala Pro Arg Val Arg Glu Leu Leu Leu Asp
        195                 200                 205

Ala Leu Ser Pro Glu Gln Leu Val Leu Thr Leu Leu Glu Ala Glu Pro
    210                 215                 220

Pro His Val Leu Ile Ser Arg Pro Ser Ala Pro Phe Thr Glu Ala Ser
225                 230                 235                 240

Met Met Met Ser Leu Thr Lys Leu Ala Asp Lys Glu Leu Val His Met
                245                 250                 255

Ile Ser Trp Ala Lys Lys Ile Pro Gly Phe Val Glu Leu Ser Leu Phe
            260                 265                 270

Asp Gln Val Arg Leu Leu Glu Ser Cys Trp Met Glu Val Leu Met Met
        275                 280                 285

Gly Leu Met Trp Arg Ser Ile Asp His Pro Gly Lys Leu Ile Phe Ala
    290                 295                 300

Pro Asp Leu Val Leu Asp Arg Asp Glu Gly Lys Cys Val Glu Gly Ile
305                 310                 315                 320

Leu Glu Ile Phe Asp Met Leu Leu Ala Thr Thr Ser Arg Phe Arg Glu
                325                 330                 335

Leu Lys Leu Gln His Lys Glu Tyr Leu Cys Val Lys Ala Met Ile Leu
            340                 345                 350
```

```
Leu Asn Ser Ser Met Tyr Pro Leu Val Thr Ala Thr Gln Asp Ala Asp
            355                 360                 365

Ser Ser Arg Lys Leu Ala His Leu Leu Asn Ala Val Thr Asp Ala Leu
    370                 375                 380

Val Trp Val Ile Ala Lys Ser Gly Ile Ser Ser Gln Gln Gln Ser Met
385                 390                 395                 400

Arg Leu Ala Asn Leu Leu Met Leu Leu Ser His Val Arg His Ala Arg
                405                 410                 415

Ser Ala

<210> SEQ ID NO 22
<211> LENGTH: 34
<212> TYPE: DNA
<213> ORGANISM: Homo sapiens

<400> SEQUENCE: 22
cttggatcca tagccctgct gtgatgaatt acag                              34

<210> SEQ ID NO 23
<211> LENGTH: 33
<212> TYPE: DNA
<213> ORGANISM: Homo sapiens

<400> SEQUENCE: 23
gatggatcct cacctcaggg ccaggcgtca ctg                               33

<210> SEQ ID NO 24
<211> LENGTH: 1898
<212> TYPE: DNA
<213> ORGANISM: Homo sapiens

<400> SEQUENCE: 24
cacgaatctt tgagaacatt ataatgacct ttgtgcctct tcttgcaagg tgttttctca    60
gctgttatct caagacatgg atataaaaaa ctcaccatct agccttaatt ctccttcctc   120
ctacaactgc agtcaatcca tcttacccct ggagcacggc tccatataca taccttcctc   180
ctatgtagac agccaccatg aatatccagc catgacattc tatagccctg ctgtgatgaa   240
ttacagcatt cccagcaatg tcactaactt ggaaggtggg cctggtcggc agaccacaag   300
cccaaatgtg ttgtggccaa cacctgggca cctttctcct ttagtggtcc atcgccagtt   360
atcacatctg tatgcggaac ctcaaaagag tccctggtgt gaagcaagat cgctagaaca   420
caccttacct gtaaacagag agacactgaa aaggaaggtt agtgggaacc gttgcgccag   480
ccctgttact ggtccaggtt caaagaggga tgctcacttc tgcgctgtct gcagcgatta   540
cgcatcggga tatcactatg gagtctggtc gtgtgaagga tgtaaggcct tttttaaaag   600
aagcattcaa ggcataatg attatatttg tccagctaca aatcagtgta caatcgataa    660
aaaccggcgc aagagctgcc aggcctgccg acttcggaag tgttacgaag tgggaatggt   720
gaagtgtggc tcccggagag agagatgtgg gtaccgcctt gtgcggagac agagaagtgc   780
cgacgagcag ctgcactgtg ccggcaaggc caagagaagt ggcggccacg cgccccgagt   840
gcgggagctg ctgctggacg ccctgagccc cgagcagcta gtgctcaccc tcctggaggc   900
tgagccgccc catgtgctga tcagccgccc cagtgcgccc ttcaccgagg cctccatgat   960
gatgtccctg accaagttgg ccgacaagga gttggtacac atgatcagct gggccaagaa  1020
gattcccggc tttgtggagc tcagcctgtt cgaccaagtg cggctcttgg agagctgttg  1080
gatggaggtg ttaatgatgg ggctgatgtg gcgctcaatt gaccaccccg gcaagctcat  1140
```

-continued

```
ctttgctcca gatcttgttc tggacaggga tgaggggaaa tgcgtagaag gaattctgga    1200
aatctttgac atgctcctgg caactacttc aaggtttcga gagttaaaac tccaacacaa    1260
agaatatctc tgtgtcaagg ccatgatcct gctcaattcc agtatgtacc ctctggtcac    1320
agcgacccag gatgctgaca gcagccggaa gctggctcac ttgctgaacg ccgtgaccga    1380
tgctttggtt tgggtgattg ccaagagcgg catctcctcc cagcagcaat ccatgcgcct    1440
ggctaacctc ctgatgctcc tgtcccacgt caggcatgcg agtaacaagg catggaaca    1500 tctgctcaac atgaagtgca aaatgtggt cccagtgtat gacctgctgc tggagatgct    1560
gaatgcccac gtgcttcgcg ggtgcaagtc ctccatcacg gggtccgagt gcagcccggc    1620
agaggacagt aaaagcaaag agggctccca gaacccacag tctcagtgac gcctggccct    1680
gaggtgaact ggcccacaga ggtcacaagc tgaagcgtga actccagtgt gtcaggagcc    1740
tgggcttcat ctttctgctg tgtggtccct catttggtga tggcaggctt ggtcatgtac    1800
catccttccc tccaccttcc caactctcag gagtcggtgt gaggaagcca tagtttccct    1860
tgttagcaga gggacatttg aatcgagcgt ttccacac                             1898
```

<210> SEQ ID NO 25
<211> LENGTH: 530
<212> TYPE: PRT
<213> ORGANISM: Homo sapiens

<400> SEQUENCE: 25

```
Met Asp Ile Lys Asn Ser Pro Ser Ser Leu Asn Ser Pro Ser Ser Tyr
1               5                   10                  15

Asn Cys Ser Gln Ser Ile Leu Pro Leu Glu His Gly Ser Ile Tyr Ile
            20                  25                  30

Pro Ser Ser Tyr Val Asp Ser His His Glu Tyr Pro Ala Met Thr Phe
        35                  40                  45

Tyr Ser Pro Ala Val Met Asn Tyr Ser Ile Pro Ser Asn Val Thr Asn
    50                  55                  60

Leu Glu Gly Gly Pro Gly Arg Gln Thr Thr Ser Pro Asn Val Leu Trp
65                  70                  75                  80

Pro Thr Pro Gly His Leu Ser Pro Leu Val Val His Arg Gln Leu Ser
                85                  90                  95

His Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Val
        115                 120                 125

Ser Gly Asn Arg Cys Ala Ser Pro Val Thr Gly Pro Gly Ser Lys Arg
    130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Leu Val Arg Arg Gln Arg Ser Ala Asp Glu Gln Leu His
225                 230                 235                 240
```

```
Cys Ala Gly Lys Ala Lys Arg Ser Gly Gly His Ala Pro Arg Val Arg
                245                 250                 255
Glu Leu Leu Leu Asp Ala Leu Ser Pro Glu Gln Leu Val Leu Thr Leu
            260                 265                 270
Leu Glu Ala Glu Pro Pro His Val Leu Ile Ser Arg Pro Ser Ala Pro
        275                 280                 285
Phe Thr Glu Ala Ser Met Met Met Ser Leu Thr Lys Leu Ala Asp Lys
    290                 295                 300
Glu Leu Val His Met Ile Ser Trp Ala Lys Lys Ile Pro Gly Phe Val
305                 310                 315                 320
Glu Leu Ser Leu Phe Asp Gln Val Arg Leu Leu Glu Ser Cys Trp Met
                325                 330                 335
Glu Val Leu Met Met Gly Leu Met Trp Arg Ser Ile Asp His Pro Gly
                340                 345                 350
Lys Leu Ile Phe Ala Pro Asp Leu Val Leu Asp Arg Asp Glu Gly Lys
                355                 360                 365
Cys Val Glu Gly Ile Leu Glu Ile Phe Asp Met Leu Leu Ala Thr Thr
        370                 375                 380
Ser Arg Phe Arg Glu Leu Lys Leu Gln His Lys Glu Tyr Leu Cys Val
385                 390                 395                 400
Lys Ala Met Ile Leu Leu Asn Ser Ser Met Tyr Pro Leu Val Thr Ala
                405                 410                 415
Thr Gln Asp Ala Asp Ser Ser Arg Lys Leu Ala His Leu Leu Asn Ala
            420                 425                 430
Val Thr Asp Ala Leu Val Trp Val Ile Ala Lys Ser Gly Ile Ser Ser
        435                 440                 445
Gln Gln Gln Ser Met Arg Leu Ala Asn Leu Leu Met Leu Leu Ser His
    450                 455                 460
Val Arg His Ala Ser Asn Lys Gly Met Glu His Leu Leu Asn Met Lys
465                 470                 475                 480
Cys Lys Asn Val Val Pro Val Tyr Asp Leu Leu Leu Glu Met Leu Asn
                485                 490                 495
Ala His Val Leu Arg Gly Cys Lys Ser Ser Ile Thr Gly Ser Glu Cys
                500                 505                 510
Ser Pro Ala Glu Asp Ser Lys Ser Lys Glu Gly Ser Gln Asn Pro Gln
            515                 520                 525
Ser Gln
    530

<210> SEQ ID NO 26
<211> LENGTH: 30
<212> TYPE: DNA
<213> ORGANISM: Homo sapiens

<400> SEQUENCE: 26
gtgcggatcc tctcaagaca tggatataaa                                        30

<210> SEQ ID NO 27
<211> LENGTH: 25
<212> TYPE: DNA
<213> ORGANISM: Homo sapiens

<400> SEQUENCE: 27
agtaacaggg ctggcgcaac ggttc                                             25
```

```
<210> SEQ ID NO 28
<211> LENGTH: 22
<212> TYPE: DNA
<213> ORGANISM: Homo sapiens

<400> SEQUENCE: 28
actggcgatg gaccactaaa gg                                              22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
gatgggctta ctgaccaacc                                                 20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
agatgctcca tgcctttg                                                   18

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
ttcaccgagg cctccatgat g                                               21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
cagatgttcc atgcccttgt t                                               21
```